US012727929B2

(12) United States Patent
Rains

(10) Patent No.: US 12,727,929 B2
(45) Date of Patent: Sep. 8, 2026

(54) CRYOSURGERY COOLANT DELIVERY SYSTEM AND METHOD OF PREPARING AND USING THE SAME

(71) Applicant: Cool Renewal, LLC, Nashville, TN (US)

(72) Inventor: Ashley Lindsey Rains, Brentwood, TN (US)

(73) Assignee: COOL RENEWAL, LLC, Nashville, TN (US)

( * ) Notice: Subject to any disclaimer, the term of this patent is extended or adjusted under 35 U.S.C. 154(b) by 398 days.

(21) Appl. No.: 18/331,729

(22) Filed: Jun. 8, 2023

(65) Prior Publication Data

US 2023/0397944 A1 Dec. 14, 2023

Related U.S. Application Data

(60) Provisional application No. 63/350,652, filed on Jun. 9, 2022.

(51) Int. Cl.

| | |
|---|---|
| ***F25B 41/40*** | (2021.01) |
| ***A61B 18/02*** | (2006.01) |
| ***C09K 5/04*** | (2006.01) |

(52) U.S. Cl.

CPC .......... *A61B 18/0218* (2013.01); *C09K 5/045* (2013.01); *F25B 41/40* (2021.01); *C09K 2205/122* (2013.01); *C09K 2205/126* (2013.01); *C09K 2205/22* (2013.01)

(58) Field of Classification Search

CPC ........ A61B 18/0218; A61B 2018/0275; C09K 5/045; C09K 2205/122; C09K 2205/126; C09K 2205/22; F25B 41/40; F25B 19/005; F25B 2400/121

See application file for complete search history.

(56) References Cited

U.S. PATENT DOCUMENTS

| | | | | |
|---|---|---|---|---|
| 4,646,735 | A * | 3/1987 | Seney | A61M 19/00 606/22 |
| 7,238,299 | B2 | 7/2007 | Singh et al. | |
| 8,066,698 | B2 | 11/2011 | Howlett et al. | |
| 9,074,115 | B2 | 7/2015 | Low | |
| 11,154,874 | B2 | 10/2021 | Young et al. | |
| 11,172,975 | B2 | 11/2021 | Niedbala et al. | |

(Continued)

FOREIGN PATENT DOCUMENTS

| | | |
|---|---|---|
| CN | 106821588 A | 12/2019 |
| CN | 213851005 U | 8/2021 |

*Primary Examiner* — William J Levicky
*Assistant Examiner* — Joshua Brendon Solomon
(74) *Attorney, Agent, or Firm* — Womble Bond Dickinson (US) LLP

(57) ABSTRACT

A cryosurgery coolant delivery system may include a canister body defining an inner chamber, a canister head portion coupled to the canister, and a coolant contained in the inner chamber. The coolant may include a mixture of 1,1,1,2-tetrafluoroethane (HFC-134a), 2,3,3,3-tetrafluoropropene (HFO-1234yf), pentafluoroethane (HFC-125), and difluoromethane (HFC-32). In other aspects, the coolant may include a mixture of difluoromethane (HFC-32), pentafluoroethane (HFC-125), 1,1,1,2-tetrafluoroethane (HFC-134a), 2,3,3,3-Tetrafluoroprop-1-ene (HFO-1234yf), and trans-1,3,3,3-Tetrafluoroprop-1-ene.

20 Claims, 7 Drawing Sheets

(56) References Cited

U.S. PATENT DOCUMENTS

2010/0127209 A1* 5/2010 Singh ........................ C08J 9/122
252/68
2020/0109000 A1* 4/2020 Martin .................... B65D 83/40
2020/0146739 A1* 5/2020 Klever ................ A61M 15/009
2020/0188939 A1* 6/2020 Young ........................ B05B 1/02

* cited by examiner 402
400
404

302
300
304

204
200
202
204

CRYOSURGERY COOLANT DELIVERY SYSTEM AND METHOD OF PREPARING AND USING THE SAME

CROSS-REFERENCE TO RELATED APPLICATION

This application claims the benefit of and priority to U.S. Provisional Patent Application No. 63/350,652 filed Jun. 9, 2022, the entire contents of which are incorporated by reference herein.

BACKGROUND

Cryosurgery is an alternative to surgical excision or scalpel removal that involves subjecting abnormal tissues or lesions on or near the surface of a patient's skin to sufficiently low temperatures to destroy the tissue/lesion. In a cryosurgical procedure, a coolant or cryogen is applied to the desired location of a patient's skin surface to freeze and destroy the tissue. The tissue subsequently forms a scab and is sloughed off to allow for the growth of new healthy tissue. Cryosurgery is minimally invasive, providing reduced pain and recovery time in comparison to traditional scalpel removal.

Liquid nitrogen is commonly used as a coolant for cryosurgical procedures. However, use of liquid nitrogen requires expensive and heavy, non-portable equipment to store and administer the treatment, and may be prone to loss from evaporation if stored improperly. Refills of liquid nitrogen storage tanks must be scheduled with a gas delivery service, which may increase costs and be an inconvenience to care providers. Alternatively, refrigerants such as hydrofluorocarbons (e.g., freon) may be used as a cryosurgery coolant. However, many of these refrigerants are harmful to the environment, and are increasingly the subject of phase-out regulations, leading to decreases in production and supply that in turn increase costs and issues with sourcing. Cryosurgery systems including coolants and containers that meet current applicable transport, environmental, and safety regulations, and methods of use, would be beneficial.

SUMMARY

Embodiments of the present disclosure may include a cryosurgery coolant delivery system. The cryosurgery coolant delivery system may include a canister body defining an inner chamber, a canister head portion coupled to the canister body, and a coolant contained in the inner chamber. The canister head portion may include a trigger actuator, an outlet, and an outlet channel in fluid communication with the outlet and the inner chamber of the canister body. The coolant may include a mixture of 1,1,1,2-tetrafluoroethane (HFC-134a), 2,3,3,3-tetrafluoropropene (HFO-1234yf), pentafluoroethane (HFC-125), and difluoromethane (HFC-32). In other aspects, the coolant may include a mixture of difluoromethane (HFC-32), pentafluoroethane (HFC-125), 1,1,1,2-tetrafluoroethane (HFC-134a), 2,3,3,3-Tetrafluoroprop-1-ene (HFO-1234yf), and trans-1,3,3,3-Tetrafluoroprop-1-ene.

In accordance with further aspects of the present disclosure, a method of administering a coolant for cryosurgical applications is provided. The method may include identifying a location of a patient's skin surface to be treated, actuating a trigger of a cryosurgery coolant delivery system, whereby an outlet of a head portion of the cryosurgery coolant delivery system sprays a coolant, and applying the coolant to the skin surface.

BRIEF DESCRIPTION OF THE SEVERAL VIEWS OF THE DRAWINGS

A more particular description will be rendered by reference to exemplary embodiments that are illustrated in the accompanying figures. Understanding that these drawings depict exemplary embodiments and do not limit the scope of this disclosure, the exemplary embodiments will be described and explained with additional specificity and detail through the use of the accompanying drawings in which.

Figure 1:
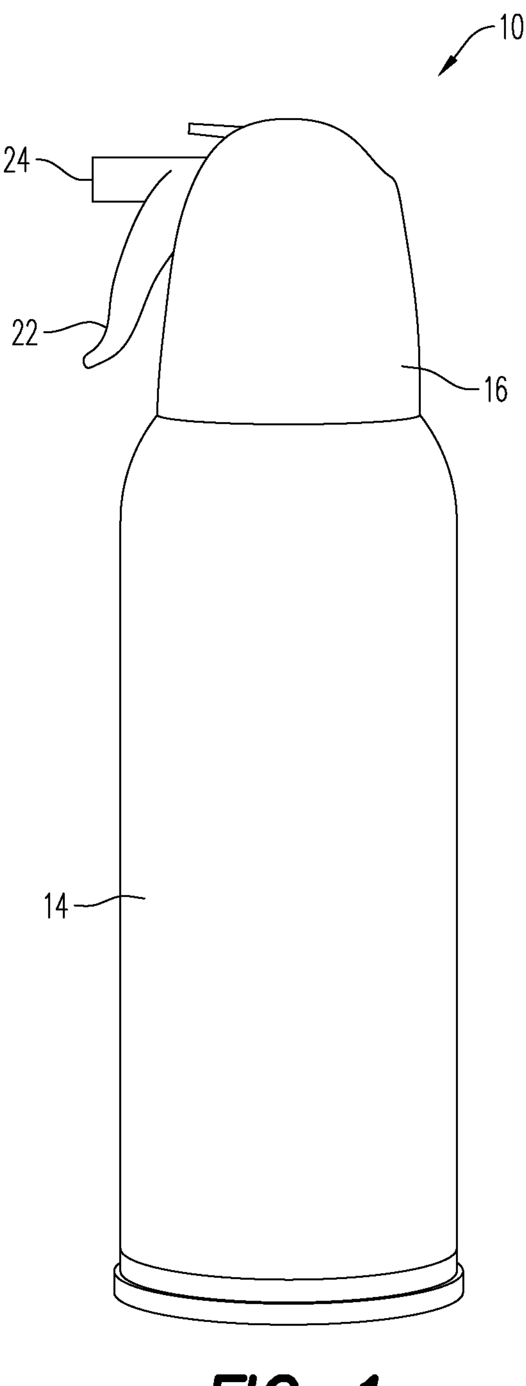
FIG. 1 illustrates a front view of a cryosurgery coolant delivery system, in accordance with an embodiment.

Various features, aspects, and advantages of the exemplary embodiments will become more apparent from the following detailed description, along with the accompanying drawings in which like numerals represent like components throughout the figures and detailed description. The various described features are not necessarily drawn to scale in the drawings but are drawn to aid in understanding the features of the exemplary embodiments.

The headings used herein are for organizational purposes only and are not meant to limit the scope of the disclosure or the claims. To facilitate understanding, reference numerals have been used, where possible, to designate like elements common to the figures.

DETAILED DESCRIPTION

Reference will now be made in detail to various exemplary embodiments. Each example is provided by way of explanation and is not meant as a limitation and does not constitute a definition of all possible embodiments. It is understood that reference to a particular "exemplary embodiment" of, e.g., a structure, assembly, component, configuration, method, etc. includes exemplary embodiments of, e.g., the associated features, subcomponents, method steps, etc. forming a part of the "exemplary embodiment".

Figure 2:
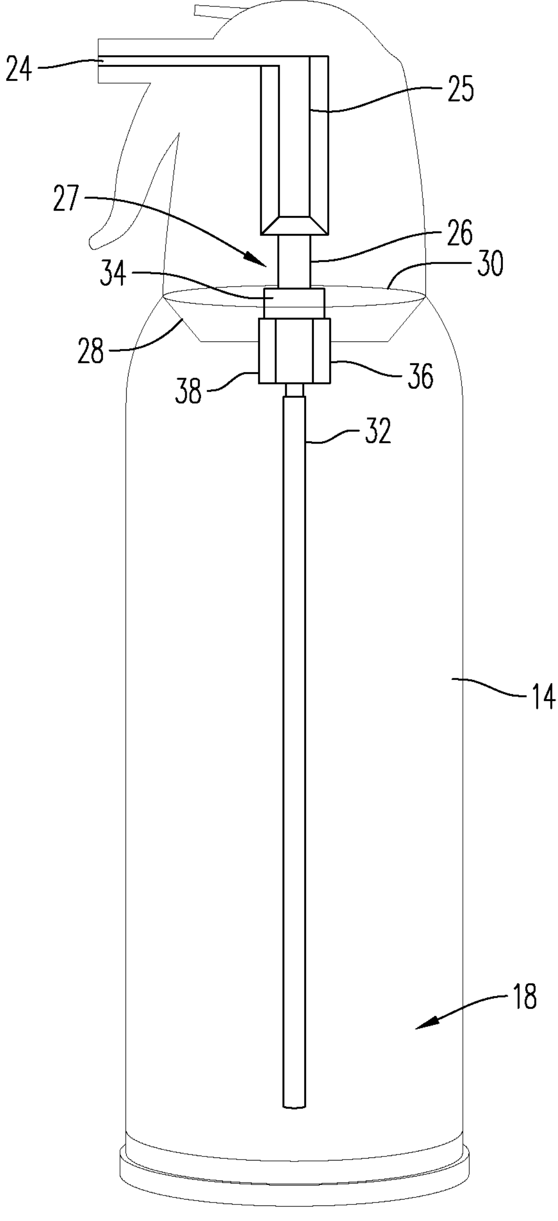
FIG. 2 illustrates a front view of the cryosurgery coolant delivery system of FIG. 1 with a canister body and a canister head portion thereof being shown as transparent to reveal internal components of the cryosurgery coolant delivery system.
Figure 3:
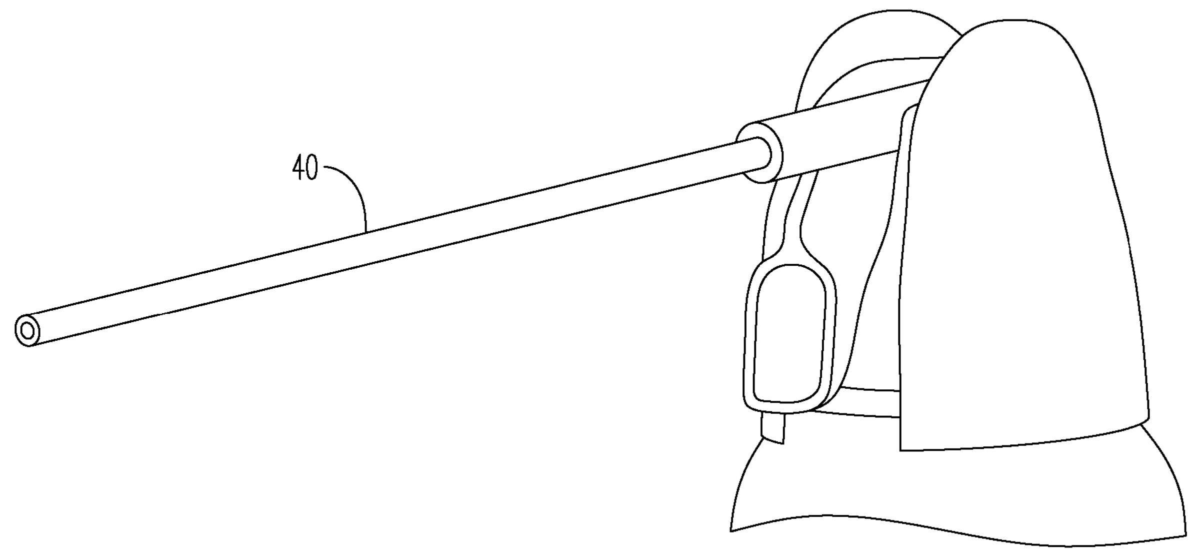
FIG. 3 illustrates a front, perspective view of the canister head portion and an extender tube of the cryosurgery coolant delivery system of FIG. 1.

In an embodiment, with reference to FIGS. 1-3, a cryosurgery coolant delivery system 10 may include a canister body 14, a canister head portion 16 coupled to the canister body 14, and a coolant (not explicitly shown) contained in the canister body 14. The coolant may be applied to a patient's skin surface at a desired location for treatment to destroy abnormal tissues, such as lesions including verruca (warts) including plantar warts, seborrheic keratosis, actinic keratosis, achrochordon (skin tags), molluscum contagiosum, lentigo (age spots), dermatofibroma, small keloids, granuloma annulare, porokeratosis plantaris, angiomas, keratoacanthoma, chondrodermatitis, epithelial nevus, leukoplakia, granuloma pyogenicum, and pyogenic granuloma.

The coolant may include a mixture of at least one hydrofluoroolefin and at least one hydrofluorocarbon. The coolant may include one or more of 1,1,1,2-tetrafluoroethane (ASHRAE Standard 34 designation HFC-134a), 2,3,3,3-tetrafluoropropene (HFO-1234yf), pentafluoroethane (HFC-125), and difluoromethane (HFC-32). In an aspect, the percent concentration (w/w) of the coolant mixture may be about 25.7% 1,1,1,2-tetrafluoroethane (HFC-134a), about 25.3% 2,3,3,3-tetrafluoropropene (HFO-1234yf), about 24.7% pentafluoroethane (HFC-125), and about 24.3% difluoromethane (HFC-32).

In another embodiment, the coolant delivered by the cryosurgery coolant delivery system 10 may be a coolant mixture (e.g., a liquefied gas) including difluoromethane (HFC-32), pentafluoroethane (HFC-125), 1,1,1,2-tetrafluoroethane (HFC-134a), 2,3,3,3-Tetrafluoroprop-1-ene (HFO-1234yf), and trans-1,3,3,3-Tetrafluoroprop-1-ene. In an aspect, the percent concentration (w/w) of the coolant mixture may be about 26.00% difluoromethane, about 26.00% pentafluoroethane, about 21.00% 1,1,1,2-Tetrafluoroethane, about 20.00% 2,3,3,3-tetrafluoroprop-1-ene, and about 7.00% trans-1,3,3,3-Tetrafluoroprop-1-ene.

With continued reference to FIGS. 1 and 2, the canister body 14 defines an inner chamber 18 for storing the coolant, and the canister head portion 16 may further include a trigger 22 and an outlet 24 in fluid communication with the inner chamber 18 of the canister body 14. The canister body 14 may be formed from any suitable material(s) and have any dimensions, as applications require, consistent with this disclosure. For example, the canister body 14 may be formed from a material and be dimensioned to meet Department of Transportation regulations covering compressed gases and/or refrigerant gases. In an aspect, the canister body 14 may be fabricated from stainless steel or aluminum.

The canister head portion 16 contains an outlet channel 25 in fluid communication with the outlet 24, which receives an end portion of a valve stem 26 of a valve assembly 27. The valve assembly 27 includes a valve housing 28 connected to the valve stem 26 and provided generally at a top, e.g., nearest the canister head portion 16, of the canister body 14 or a canister opening 30. The valve housing 28 is connected to a dip tube 32 which extends into the inner chamber 18 of the canister body 14. The valve assembly 27 further includes a valve gasket 34 provided in the valve housing 28, a spring housing 38 positioned within the valve housing 28, and a spring 36 provided in the spring housing 38.

In use, the trigger 22 is actuated (e.g., squeezed), whereby the valve stem 26 presses against the valve gasket 34 to compress the spring 36. Upon actuation, the valve assembly 27 opens a flow path from the inner chamber 18 of the canister body 14 through, in turn, the dip tube 32, the valve stem 26, the outlet channel 25, and the outlet 24. The pressurized coolant provided in the inner chamber 18 of the canister body 14 is passed through one or more openings in the dip tube 32, through the flow path, and out of the outlet 24 to the outside environment.

In an aspect, the outlet channel 25, the outlet 24, and the valve assembly 27 (and other components of the system 10) may be dimensioned, without limitation, consistently with the canister head portion 16, the canister body 14, and open interior dimensions, including the canister opening dimensions, for operability of the canister and compliance with applicable regulations. For example, the dip tube 32 may have a length corresponding to the distance between the canister opening 30 and a bottom wall of the canister body 14. The canister body 14 may be filled with the coolant, sealed, and pressurized according to known methods. An extender tube 40, shown in FIG. 3, may be inserted into the outlet 24 to extend the flowpath of the coolant system externally of and away from the canister head portion 16.

A method of administering the coolant for cryosurgical applications may include identifying and isolating a location of a patient's skin surface to be treated. The coolant may then be applied to the skin surface and allowed to evaporate. To apply the coolant, the trigger 22 may be actuated to open the flow path between the inner chamber 18 of the canister body 14 and the outside environment to allow the cryosurgical coolant to flow out of the canister head portion 16 and onto the surface to be treated (e.g., the location of the skin surface).

In an aspect, the coolant delivery system 10 may include accessory devices or applicators configured for targeted delivery to a surface for cooling as discussed further below with respect to FIGS. 4-7. The applicator may be selected based on factors including the size and/or the location of the skin surface to be treated.

Figure 4:
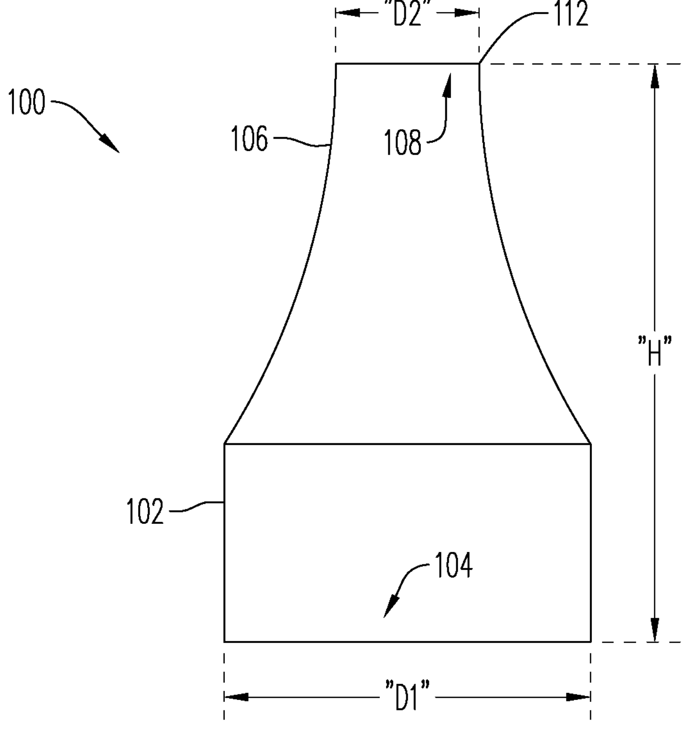
FIG. 4 illustrates a longitudinal cross-sectional view of an isolation funnel applicator for use with the cryosurgery coolant delivery system of FIG. 1.
Figures 5A, 5B, 5C, 5D, 5E:
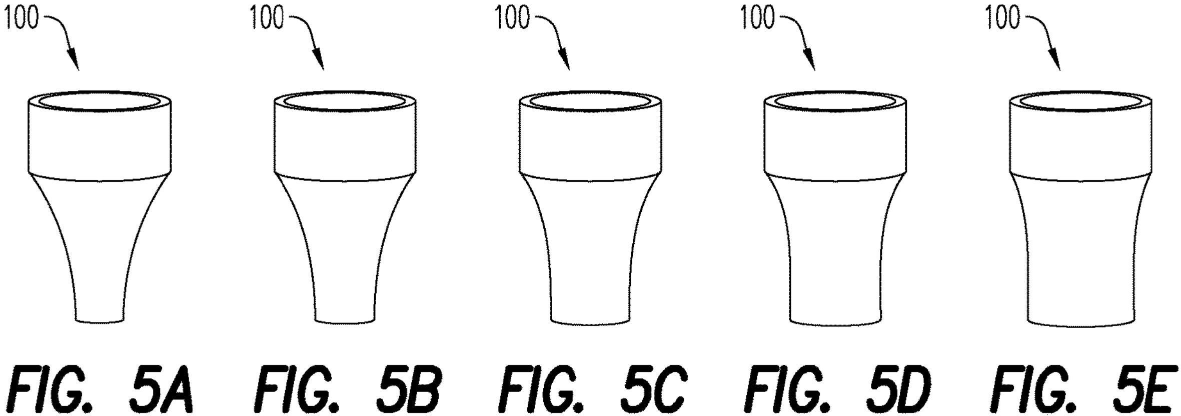
FIGS. 5A-5E illustrate a plurality of isolation funnel applicators for use with the cryosurgery coolant delivery system of FIG. 1.

FIG. 4 shows an isolation funnel applicator 100 for use with the cryosurgery coolant delivery system 10 of FIGS. 1-3. The isolation funnel applicator 100 may be used to treat fleshy tissues on the body excluding the head and neck. The isolation funnel applicator 100 may include a funnel wall 102 defining a funnel inlet opening 104, and a funnel neck 106 extending from the funnel wall 102 and defining a funnel outlet opening 108. The funnel outlet opening 108 may have a smaller diameter "D2" than a diameter "D1" of the funnel inlet opening 104. The funnel neck 106 may be configured to be positioned against the skin surface to be treated so that an end surface 112 of the funnel neck 106 surrounds the surface area to be treated. The cryosurgery coolant may then be sprayed directly onto the skin enclosed by the end surface 112 through the funnel inlet opening 104. The coolant may be sprayed for a duration of time, for example, between about 3 seconds and about 6 seconds, or until a layer of coolant has accumulated in the isolation funnel application 100 having a depth of between about ⅛-inch to about ¼-inch. A tight seal between the skin surface and end surface 112 contacting the skin may prevent migration of the cryosurgery coolant to areas adjacent to the surface area being treated. The isolation funnel applicator 100 may be removed after the coolant has evaporated.

The dimensions of the isolation funnel applicator 100 may vary, without limitation, as applications require. For example, the diameter "D1" of the funnel inlet opening 104 may be selected to receive the cryogenic fluid from the outlet 24 of the canister body 14, the diameter "D2" of the funnel outlet opening 108 may be selected to correspond to a surface area to be treated, and a height "H" or length of the isolation funnel application 100 may be selected to ensure, e.g., a sufficient volume of coolant for delivery to the skin surface. Various exemplary geometries of the isolation funnel applicator 100 are shown in FIGS. 5A-5E.

Figures 6A, 6B, 6C:
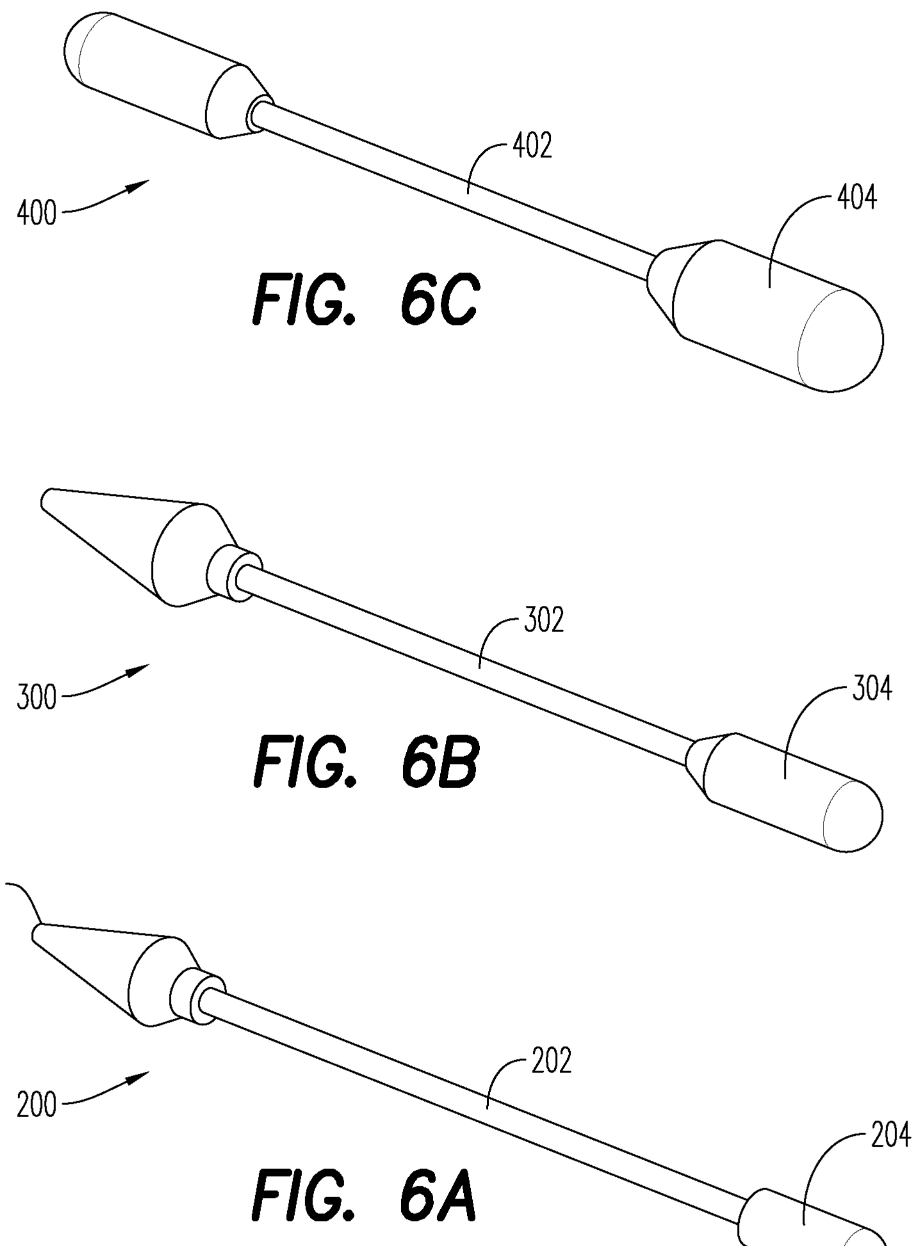
FIGS. 6A-6C illustrate a plurality of foam tip applicators for use with the cryosurgery coolant delivery system of FIG. 1.

FIGS. 6A-6C show exemplary foam-tipped applicators 200, 300, 400 with different tip profiles for use with the cryosurgery coolant delivery system 10. Foam-tipped applicators may be used to treat areas that are hard to reach, bony surfaces, or treatment areas on the head, face, or neck.

Each of the foam-tipped applicators 200, 300, 400 may respectively include a hollow stick 202, 302, 402 with a bud tip 204, 304, 404 provided on each end of the respective hollow stick 202, 302, 402. The hollow stick 202, 302, 402 may be made from a polypropylene plastic and the bud tips 204, 304, 404 may be made from a polyester polyurethane foam, and may include an internal cotton layer. A method of using the foam-tipped applicators 200, 300, 400 may include applying the cryosurgery coolant to the bud tip 204, 304, 404 of the applicator 200, 300, 400 until the bud tip 204, 304, 404 is saturated. The applicator 200, 300, 400 may be rotated to ensure complete saturation of the bud tip 204, 304, 404. The coolant applied to the bud tip 204, 304, 404 will cause the bud tip 204, 304, 404 to become frozen and crystallize after approximately 10 seconds. The saturated bud tip 204, 304, 404 may then be applied directly to the surface area to be treated for a duration of time, for example between about 20 and 40 seconds. The duration of application may depend on factors including the size and location of the area to be treated.

The size of the foam-tipped applicator 200, 300, 400 may vary, without limitation, as applications require. The foam-tipped applicator 200, 300, 400 may also be provided in a variety of bud tip shapes. For example, the bud tip 204 may have a rounded profile or a pointed profile. In an aspect, as shown in FIG. 6A, one of the bud tips 204 of the foam-tipped applicator 200 may have a rounded profile and the other of the bud tips 204 of the foam-tipped applicator 200 may have a pointed profile.

Figure 7:
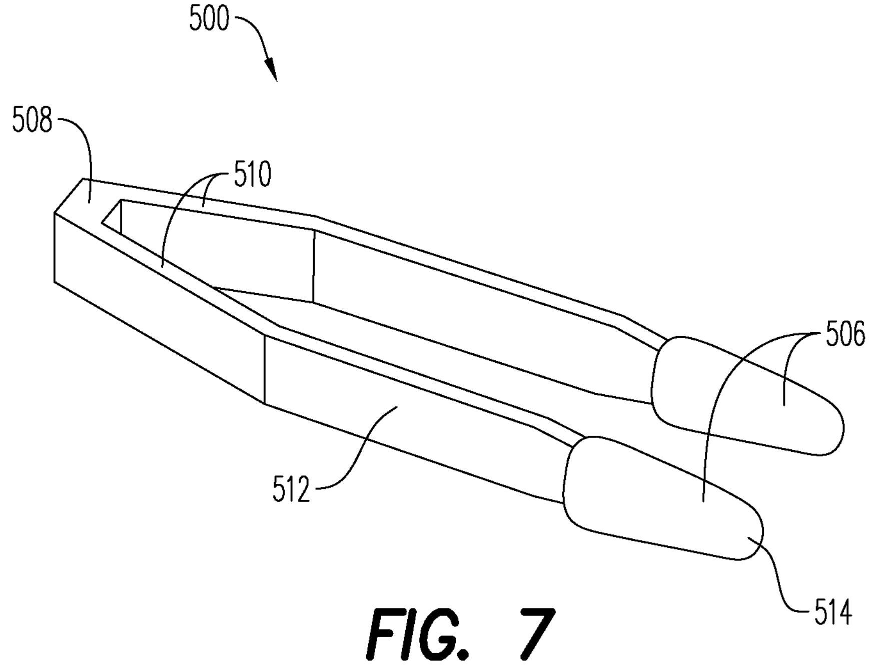
FIG. 7 illustrates a tweezer for use with the cryosurgery coolant delivery system of FIG. 1.

FIG. 7 shows a pair of tweezers 500 for use with the cryosurgery coolant delivery system 10 of FIGS. 1-3 in the treatment of skin tags anywhere on the body. The tweezers 500 may be made from acrylonitrile butadiene styrene copolymer plastic (ABS) and may include two foam tips 514 provided on each free end 506 of the tweezers 500. The tweezers 500 may include a base 508 joining two arms 510 that each terminate in a respective free end 506. A grip section 512 may be provided along a mid-section of each arm 510 and having a tactile or textured surface for ease of handling and use. The free end 506 of each tweezer arm 510 may be biased away from one another and radially outward from and by the base 508 so that the free ends 506 contact one another upon pressing the arms 510 together. Each free end 506 of the tweezers 500 is provided with the foam tip 514. The foam tip 514 may be made from a polyester polyurethane foam and may include an internal cotton layer.

A method of using the tweezers 500 may include applying the cryosurgery coolant to the foam tips 514 of the tweezers 500 until the tips 514 are saturated. The tweezers 500 may be rotated to ensure complete saturation of the tips 514. The coolant applied to the tips 514 will cause the tips 514 to become frozen and crystallize after approximately 10 seconds. The saturated tips 514 may then be applied directly to the surface area to be treated for a duration of time, for example between about 20 seconds and about 40 seconds. The tweezers 500 may be applied directly to the skin tag lesion for a duration of time, for example between about 20 seconds and about 40 seconds. The tweezers 500 may also be applied to the base of the stalk to eliminate blood supply to the skin tag.

This disclosure, in various embodiments, configurations and aspects, includes components, methods, processes, systems, and/or apparatuses as depicted and described herein, including various embodiments, sub-combinations, and subsets thereof. This disclosure contemplates, in various embodiments, configurations and aspects, the actual or optional use or inclusion of, e.g., components or processes as may be well-known or understood in the art and consistent with this disclosure though not depicted and/or described herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. The term "about" is defined as + or −10% of the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that the appended claims should cover variations in the ranges except where this disclosure makes clear the use of a particular range in certain embodiments.

The terms "determine", "calculate" and "compute," and variations thereof, as used herein, are used interchangeably and include any type of methodology, process, mathematical operation or technique.

This disclosure is presented for purposes of illustration and description. This disclosure is not limited to the form or forms disclosed herein. In the Detailed Description of this disclosure, for example, various features of some exemplary embodiments are grouped together to representatively describe those and other contemplated embodiments, configurations, and aspects, to the extent that including in this disclosure a description of every potential embodiment, variant, and combination of features is not feasible. Thus, the features of the disclosed embodiments, configurations, and aspects may be combined in alternate embodiments, configurations, and aspects not expressly discussed above. For example, the features recited in the following claims lie in less than all features of a single disclosed embodiment, configuration, or aspect. Thus, the following claims are hereby incorporated into this Detailed Description, with each claim standing on its own as a separate embodiment of this disclosure.

Advances in science and technology may provide variations that are not necessarily express in the terminology of this disclosure although the claims would not necessarily exclude these variations.

What is claimed is:

1. A cryosurgery coolant delivery system, comprising:
- a canister body defining an inner chamber;
- a canister head portion coupled to the canister body and including a trigger actuator, an outlet, and an outlet channel in fluid communication with the outlet and the inner chamber of the canister body; and
- a coolant contained in the inner chamber, the coolant including a mixture of 1,1,1,2-tetrafluoroethane (HFC-134a), 2,3,3,3-tetrafluoropropene (HFO-1234yf), pentafluoroethane (HFC-125), and difluoromethane (HFC-32);
- wherein a percent concentration (w/w) of the coolant is about 25.7% 1,1,1,2-tetrafluoroethane (HFC-134a), about 25.3% 2,3,3,3-tetrafluoropropene (HFO-1234yf), about 24.7% pentafluoroethane (HFC-125), and about 24.3% difluoromethane (HFC-32).

2. The cryosurgery coolant delivery system of claim 1, further comprising:
- a valve stem extending from the outlet channel;
- a valve gasket extending from the valve stem;
- a spring coupled to the valve gasket; and
- a dip tube provided between the outlet and the inner chamber, wherein the outlet, the outlet channel, the valve stem, and the dip tube provide a flow path for the coolant between the inner chamber and the outlet.

3. The cryosurgery coolant delivery system of claim 1, further comprising an extender tube configured to detachably couple to the outlet, wherein the extender tube, the outlet, and the outlet channel provide a flow path for the coolant between the interior chamber and the extender tube.

4. A cryosurgery coolant delivery system, comprising:
- a canister body defining an inner chamber;
- a canister head portion coupled to the canister body and including a trigger actuator, an outlet, and an outlet channel in fluid communication with the outlet and the inner chamber of the canister body; and
- a coolant contained in the inner chamber, the coolant including a mixture of difluoromethane (HFC-32), pentafluoroethane (HFC-125), 1,1,1,2-tetrafluoroethane (HFC-134a), 2,3,3,3-Tetrafluoroprop-1-ene (HFO-1234yf), and trans-1,3,3,3-Tetrafluoroprop-1-ene;
- wherein a percent concentration (w/w) of the coolant is about 26.00% difluoromethane, about 26.00% pentafluoroethane, about 21.00% 1,1,1,2-Tetrafluoroethane, about 20.00% 2,3,3,3-tetrafluoroprop-1-ene, and about 7.00% trans-1,3,3,3-Tetrafluoroprop-1-ene.

5. The cryosurgery coolant delivery system of claim 4, further comprising:
- a valve stem extending from the outlet channel;
- a valve gasket extending from the valve stem;
- a spring coupled to the valve gasket; and
- a dip tube provided between the outlet and the inner chamber, wherein the outlet, the outlet channel, the valve stem, and the dip tube provide a flow path for the coolant between the inner chamber and the outlet.

6. The cryosurgery coolant delivery system of claim 4, further comprising an extender tube configured to detachably couple to the outlet, wherein the extender tube, the outlet, and the outlet channel provide a flow path for the coolant between the interior chamber and the extender tube.

7. A method of administering a coolant for cryosurgical applications, comprising:
- identifying a location of a patient's skin surface to be treated;
- actuating a trigger of a cryosurgery coolant delivery system, whereby an outlet of a head portion of the cryosurgery coolant delivery system sprays a coolant; and
- applying the coolant to the skin surface;
- wherein the coolant comprises:
  - a mixture of 1,1,1,2-tetrafluoroethane (HFC-134a), 2,3,3,3-tetrafluoropropene (HFO-1234yf), pentafluoroethane (HFC-125), and difluoromethane (HFC-32) wherein a percent concentration (w/w) of the coolant is about 25.7% 1,1,1,2-tetrafluoroethane (HFC-134a), about 25.3% 2,3,3,3-tetrafluoropropene (HFO-1234yf), about 24.7% pentafluoroethane (HFC-125), and about 24.3% difluoromethane (HFC-32), or
  - a mixture of difluoromethane (HFC-32), pentafluoroethane (HFC-125), 1,1,1,2-tetrafluoroethane (HFC-134a), 2,3,3,3-Tetrafluoroprop-1-ene (HFO-1234yf), and trans-1,3,3,3-Tetrafluoroprop-1-ene wherein a percent concentration (w/w) of the coolant is about 26.00% difluoromethane, about 26.00% pentafluoroethane, about 21.00% 1,1,1,2-Tetrafluoroethane, about 20.00% 2,3,3,3-tetrafluoroprop-1-ene, and about 7.00% trans-1,3,3,3-Tetrafluoroprop-1-ene.

8. The method of claim 7, further comprising:
- contacting the skin surface with an isolation funnel;
- dispensing coolant into the isolation funnel so as to accumulate the coolant within the isolation funnel;
- wherein the isolation funnel is configured to create a seal against the skin surface so as to prevent migration of the coolant outside of a targeted treatment area.

9. The method of claim 7, further comprising:
- dispensing the coolant into a foam tip of an applicator so as to saturate the foam tip and freeze the foam tip; and
- applying frozen foam tip to the skin surface to provide cryosurgical treatment to the skin surface.

10. The method of claim 7, wherein spraying the coolant includes at least one of:
- saturating a foam-tipped applicator with the coolant;
- saturating foam tips of a pair of tweezers; or
- spraying the coolant through a funnel opening of an isolation funnel positioned against the skin surface until an accumulation of the coolant is provided in the isolation funnel.

11. The method of claim 7, wherein the coolant is applied to the skin surface until blood supply to the skin surface ceases.

12. The method of claim 7, wherein the coolant is applied to the skin surface directly from the outlet.

13. The cryosurgery coolant delivery system of claim 1, further comprising an isolation funnel configured to be positioned against a patient's skin, wherein the system is configured to dispense the coolant into the isolation funnel and accumulate the coolant within the funnel to a targeted treatment area of the patent's skin; and the isolation funnel is configured to form a seal against the patient's skin so as to prevent migration of the coolant outside of the targeted treatment area.

14. The cryosurgery coolant delivery system of claim 1, further comprising an applicator having a foam tip, wherein the system is configured to apply the coolant to the foam tip to saturate and freeze the foam tip prior to contact with a patient's skin, such that the frozen foam tip provides a cryosurgical interface for contacting the patient's skin.

15. The cryosurgery coolant delivery system of claim 4, further comprising an isolation funnel configured to be positioned against a patient's skin, wherein the system is configured to dispense the coolant into the isolation funnel and accumulate the coolant within the funnel to a targeted treatment area of the patent's skin, and the isolation funnel is configured to form a seal against the patient's skin so as to prevent migration of the coolant outside of the targeted treatment area.

16. The cryosurgery coolant delivery system of claim 4, further comprising an applicator having a foam tip, wherein the system is configured to apply the coolant to the foam tip to saturate and freeze the foam tip prior to contact with a patient's skin, such that the frozen foam tip provides a cryosurgical interface for contacting the patient's skin.

17. The method of claim 8, wherein the coolant is dispensed into the isolation funnel for a period of time in a range of 3 seconds to 6 seconds.

18. The method of claim 8, wherein the coolant is accumulated in the isolation funnel to a depth in a range of about ⅛ inches to about ¼ inches.

19. The method of claim 9, wherein the coolant is dispensed into the foam tip for at least 10 seconds.

20. The method of claim 9, wherein the frozen foam tip is applied to the skin surface for a period of time in a range of 20 seconds to 40 seconds.

* * * * *